(12) United States Patent
Yamaguchi

(10) Patent No.: US 9,592,369 B2
(45) Date of Patent: Mar. 14, 2017

(54) BALLOON CATHETER

(75) Inventor: Youichi Yamaguchi, Settsu (JP)

(73) Assignee: KANEKA CORPORATION, Osaka-shi (JP)

( * ) Notice: Subject to any disclaimer, the term of this patent is extended or adjusted under 35 U.S.C. 154(b) by 1089 days.

(21) Appl. No.: 12/438,118

(22) PCT Filed: Aug. 21, 2007

(86) PCT No.: PCT/JP2007/066179
§ 371 (c)(1),
(2), (4) Date: Feb. 19, 2009

(87) PCT Pub. No.: WO2008/023696
PCT Pub. Date: Feb. 28, 2008

(65) Prior Publication Data
US 2010/0174235 A1    Jul. 8, 2010

(30) Foreign Application Priority Data
Aug. 21, 2006    (JP) .................................. 2006-224457

(51) Int. Cl.
*A61M 29/02* (2006.01)
*A61M 25/10* (2013.01)
(Continued)

(52) U.S. Cl.
CPC ......... *A61M 25/104* (2013.01); *A61L 29/085* (2013.01); *A61M 25/1029* (2013.01);
(Continued)

(58) Field of Classification Search
CPC ...... A61M 2025/1031; A61M 25/1027; A61M 25/1029
(Continued)

(56) References Cited

U.S. PATENT DOCUMENTS 3,503,399 A * 3/1970 Clark et al. .............. 604/102.01
5,290,306 A * 3/1994 Trotta et al. .................. 606/194
(Continued)

FOREIGN PATENT DOCUMENTS

JP    03-051059    3/1991
JP    05-137793    6/1993
(Continued)

*Primary Examiner* — Diane Yabut
(74) *Attorney, Agent, or Firm* — Kratz, Quintos & Hanson, LLP

(57) ABSTRACT

A balloon catheter having multiple tubular members, an adaptor member connected thereto and a balloon for dilation of constricted blood vessel, wherein the peeling strength of the balloon surfaces when adheres to each other is 0.06 N or more and the modulus of the balloon in the axial direction is 100 N/mm$^2$ or more, and wherein the coated resin composition contains a hydrophilic resin that is lubricating when wet. Furthermore, the outer surface of the balloon is made of a polyamide elastomer resin composition having a durometer hardness of 55 D or less. Thus, there can be provided a balloon catheter excelling in handling property, for which keeping the balloon highly penetrable through the stricture site as the accordion phenomenon of the balloon is prevented, and simultaneously preserving the other properties of the balloon (flexibility of balloon, wrapping dimension, and dilation/shrinkage response etc.).

7 Claims, 3 Drawing Sheets

(51) Int. Cl.
   *A61L 29/08* (2006.01)
   *A61M 25/01* (2006.01)
(52) U.S. Cl.
   CPC ... *A61M 25/1027* (2013.01); *A61M 2025/018* (2013.01); *A61M 2025/0183* (2013.01); *A61M 2025/1031* (2013.01); *A61M 2025/1075* (2013.01); *A61M 2025/1088* (2013.01); *A61M 2205/32* (2013.01)
(58) Field of Classification Search
   USPC ............... 606/192, 194; 604/103.08, 103.14
   See application file for complete search history.

(56) References Cited

U.S. PATENT DOCUMENTS

| | | | | |
|---|---|---|---|---|
| 5,500,180 | A * | 3/1996 | Anderson et al. | 264/532 |
| 5,509,899 | A * | 4/1996 | Fan et al. | 604/103.14 |
| 6,389,602 | B1 * | 5/2002 | Alsaffar | 2/161.7 |
| 2004/0093008 | A1 * | 5/2004 | Zamore | 606/194 |
| 2004/0181273 | A1 * | 9/2004 | Brasington et al. | 623/1.15 |
| 2004/0267280 | A1 * | 12/2004 | Nishide et al. | 606/108 |
| 2007/0142818 | A1 * | 6/2007 | Webler et al. | 604/509 |

FOREIGN PATENT DOCUMENTS

| | | |
|---|---|---|
| JP | 07-132147 | 5/1995 |
| JP | 09-111021 | 4/1997 |
| JP | 2004-298363 | 10/2004 |
| WO | WO96/09086 | 3/1996 |
| WO | WO99/17831 | 4/1999 |
| WO | WO2006/134638 | 12/2006 |

\* cited by examiner

BALLOON CATHETER

TECHNICAL FIELD

The present invention relates to a balloon catheter used in operation to dilate a living body lumen.

BACKGROUND ART

Percutaneous transluminal angioplasty is a method that has been practiced widely, for example, for treatment of stricture site or obstruction site of vascular lumen by dilation and for recovery or improvement of blood flow in coronary arteries and peripheral blood vessels. The balloon catheter used in the percutaneous transluminal angioplasty has a shaft and a balloon inflatable and deflatable freely by regulation of its inner pressure that is connected to the terminal region of the shaft, and the shaft generally has a structure in which a lumen for inserting a guide wire (guide wire lumen) and a lumen for supplying a pressurized fluid for regulation of the balloon inner pressure (inflation lumen) are formed in the shaft in the length direction.

The percutaneous transluminal coronary angioplasty (PTCA) by using such a balloon catheter is generally practiced as follows: First, a guide catheter is inserted from a puncture site such as femoral artery, brachial artery, or radial artery, while the distal end is fed via aorta into the entrance of coronary artery. Then, a guide wire inserted in the guide wire lumen is fed beyond the stricture site of coronary artery, and a balloon catheter is then inserted along the guide wire, while the balloon is delivered to the stricture site. Then, the stricture site is dilated and treated by dilation of the balloon by supply of a pressurized fluid via the inflation lumen using a device such as indeflator. After completion of the treatment of the stricture site by dilation, the PTCA is completed by deflating the balloon under reduced pressure and withdrawing it out of the body.

Each catheter described above has a structure in which a distal shaft and a proximal shaft are connected to each other and an adaptor member holding the catheter is connected to the proximal end of the proximal shaft, and such catheters are divided roughly into two groups, depending on the length of the guide wire lumen. Hereinafter, balloon catheters having a balloon connected to the distal side of the distal shaft and a port for supplying a pressurized fluid for regulation of the inner pressure of the balloon to the inflation lumen will be described as examples.

One is an over-the-wire catheter (OTW catheter) having a guide wire lumen formed over the entire length of a catheter as shown in FIG. 1, wherein a proximal end-sided opening of guide wire lumen and an opening of inflation lumen are formed in adaptor member, a strain relief for control of flexibility in the axial direction is also formed on the adaptor member, and a distal end-sided opening of the guide wire lumen is formed in the most distal end region of balloon or to the distal side of the most distal end region of balloon. Another example thereof is a rapid exchange catheter (RX catheter) shown in FIG. 2, in which a guide wire lumen is present only on the distal side of balloon catheter and a proximal end-sided opening of the guide wire lumen is formed in the middle of the distal shaft.

Since the OTW catheter has a guide wire lumen over the entire length of the balloon catheter, it is often used for sending a guide wire to the lesion that prohibits passage of the guide wire, but the operation of withdrawing the balloon catheter while leaving the guide wire in the lesion area is rather complicated and causes problems. Thus, the OTW catheter demands additional special device and operation such as insertion of an exchange extension wire for withdrawal of the balloon catheter while the guide wire is left in the lesion.

On the other hand, the guide wire lumen is present only on the distal side of the balloon catheter in the RX catheter; thus, the convenience of operation is very favorable, as it is possible to remove, exchange, reinsert the balloon catheter easily while leaving the guide wire in the lesion area; and it is also possible to shorten the surgical period and reduce the number of devices used.

Catheters are roughly divided into two groups, depending on the shaft structure of the region having the guide wire lumen. One is a coaxial catheter, as shown by the crosssectional shape in the FIG. 4, having an inner shaft and an outer shaft coaxially surrounding the inner shaft, forming a guide wire lumen by the lumen of the inner shaft and an inflation lumen having a circular crosssectional shape between the inner shaft and the outer shaft. The other is a biaxial catheter wherein the guide wire lumen and the second lumen are arranged in parallel with each other.

In the case of an OTW catheter, the catheter generally has a coaxial or biaxial structure over the entire length. Alternatively in the case of an RX catheter, the distal shaft in the region having the guide wire lumen may have a coaxial or biaxial structure.

Various methods are disclosed for improving the convenience of operating of such catheter.

Patent Document 1 discloses a balloon catheter and a balloon having an ionic deposition film harder than the base material, formed on the surface of its stripe- or film-shaped soft resin base material.

According to the prior art, the balloon catheter and the balloon described above, if they carry an ionic deposition film formed, become flexible to a bending force, but more rigid to the force in the direction parallel to the surface, and resistant for example to buckling when the catheter is compressed. However, presence of the ionic deposition film was not effective in the insertion operation, because the film was highly vulnerable to cracking, ionically deposited substances may be released into the blood vessel, possibly showing adverse effects on the body, and the energy irradiation during ionic deposition may harden the balloon region, making it difficult to reinsert the catheter after dilation of balloon to the same or another stricture site (recross).

Patent Document 2 discloses a balloon catheter in a double-lumen structure consisting of an inner shaft and an outer shaft allowing penetration of the guide wire in the region of the catheter close to the terminal region, wherein a guide tube having an inner diameter smaller than the inner diameter of the outer shaft and larger than the outer diameter of the inner shaft is placed at least in the terminal region of the outer shaft.

According to the prior art, it is possible by installing the guide tube described above to improve the rewrap efficiency of the balloon after dilation while preventing loosening of the inner shaft, by relaxing the discontinuity in rigidity in the junction region between the outer shaft and the balloon and thus, preventing folding, to improve the insertion efficiency of the catheter in the blood vessel and the traveling efficiency thereof in the stricture site, to prevent the accordion phenomenon, and to improve the pressurization efficiency. However, installation of a guide tube on part of the inner shaft leads to generation of discontinuous change in rigidity in the region close to the guide tube and expansion of the outer diameter, increasing the wrapping size of the balloon, and thus, there are still many problems to be overcome.

Patent Document 3 discloses an OTW catheter having a first tubular part forming a guide wire lumen, a second tubular part extending in the same direction with the first tubular and having the outer face bound to the peripheral surface of the first tubular part, forming an dilation lumen, and a means of changing the flexibility of at least one of the balloon and the first and second tubular parts.

According to the prior art, in the case of a catheter having biaxial shafts described above, it is possible to select the properties of the catheter properly and thus to obtain a catheter with favorable properties, by selecting the respective components for the catheter having the first and second tubular parts and the part controlling flexibility. It is also possible to reduce cost, because the production method is simpler. However, such a catheter demands an adhesive or sleeve parts for connection of the first and second tubular parts, which leads to increase in the diameter and decrease of the flexibility of the connecting region, and thus, was not sufficiently favorable in the convenience of inserting the catheter into bent blood vessel.

Patent Document 4 discloses a long and thin catheter having an inner tubular part, an outer tubular part, and an inflatable balloon, wherein there is a second lumen formed between the inner and outer tubular parts, the inflatable balloon communicates with the second lumen, the catheter has an bonded longitudinal region for bonded between the inner and outer tubular parts, the bonded longitudinal region occupies at least 30% of the inner surface of the outer tubular part, and the inner circumference face of the catheter is bonded to the outer face of the inner tubular part.

According to the prior art, by bonding a length of the outer tubular member to the exterior of the inner member, the profile of the catheter body in at least one transverse dimension in that area is reduced and thus to reduce the diameter in the region. In addition, mutual support between the inner and outer tubular parts in the bonded longitudinal region improves the pressure transmission efficiency of the catheter. However, the bonded longitudinal region, where the inner and outer tubular parts are bonded to each other, is lower in flexibility, and thus, it was difficult to send the catheter by pushing the bonded longitudinal region through a bent blood vessel. The catheter also had a problem that the second lumen in the bonded longitudinal region was vulnerable to deformation when the bonded longitudinal region was bent, and the inflation/deflation response of the inflatable balloon was lower.

Patent Document 5 discloses a long and thin catheter having a balloon, i.e., a coaxial balloon dilation catheter, wherein the shaft of the catheter consists of an inner tube and an outer tube surrounding the inner tube, there is an inflation/deflation lumen formed between them, the inner tube is connected to the outer tube at the position distal from the proximal end region of the shaft.

In a catheter having a shaft of coaxial tubes and a balloon connected to the distal end region of the tubes, the coaxial tubes are likely to be deformed into the nested pattern when an increased resistance is applied. The balloon deforms into an accordion-like shape by deformation in a nested pattern, making the balloon more resistant to passage through a stricture site. According to the prior art, the pressure transmission efficiency of catheter is increased by connection of the distal end region of the outer tube to the inner tube. The length of the balloon in the axial direction is kept constant for prevention of the deformation of the tube into the nested pattern. It is thus possible to prevent accordion-like deformation of the balloon and retain its favorable balloon-inserting efficiency in the stricture site. However, also in the prior art, the region where the outer and inner tubes are connected is lower in flexibility, lowering the efficiency of passing the region through a bent blood vessel. In addition when the position is bent, the inflation/deflation lumen in the region deforms more easily, undesirably lowering the inflation/deflation response of the balloon.

Patent Document 1: Japanese Unexamined Patent Application Publication No. 9-111021
Patent Document 2: WO99/17831
Patent Document 3: Japanese Unexamined Patent Application Publication No. 7-132147
Patent Document 4: Japanese Unexamined Patent Application Publication No. 5-137793
Patent Document 5: Japanese Unexamined Patent Application Publication No. 3-51059

DISCLOSURE OF THE INVENTION

Technical Problems to be Solved

An object of the present invention, which was made to solve the problems above, is to realize a balloon catheter, having multiple tubular members, an adapter member connected thereto, and a balloon for dilation of constricted blood vessel, wherein the balloon catheter is free from scattering of the coating composition or the like, superior in pressure transmission efficiency allowing the force applied to the proximal-sided catheter to be conveyed efficiently to the distal region or end of the catheter while keeping the balloon flexible and without expansion in the balloon wrapping size, and highly penetrable through the stricture site, as the accordion phenomenon of the balloon and the inner shaft is prevented and the favorable inflation/deflation response of balloon is preserved simultaneously.

Means to Solve the Problems

The inventors have made an invention of a balloon catheter having multiple tubular members, an adapter member connected thereto, and a balloon for dilation of constricted blood vessel, characterized in that the peeling strength of the balloon surfaces when adheres to each other is 0.06 N or more and the modulus of the balloon in the axial direction is 100 N/mm² or more.

A balloon catheter having a balloon coated with a resin composition on the outer surface is preferable as the balloon catheter characterized as described above, and it is more preferable that the coating composition is a hydrophilic resin that becomes lubricating when wet is more preferable from the viewpoint of improvement in the insertion efficiency of the catheter in blood vessel. The hydrophilic resin preferably has a bilayer coat structure consisting of an undercoat layer containing a polyurethane resin and a topcoat layer containing a hydrophilic resin.

The outer surface of the balloon may be made of a polyamide elastomer resin composition having a durometer hardness of 55 D or less, and the balloon is more preferably made of a resin composition in a multi-layer structure.

The pressure at which the balloon folding is removed is preferably 0.6 atmG or more.

Effects of the Invention

The present invention provides a balloon catheter, comprising multiple tubular members, an adapter member connected thereto, and a balloon for dilation of constricted blood vessel, wherein the balloon catheter is free from scattering of the coating composition or the like, superior in pressure transmission efficiency allowing the force applied to the proximal-sided catheter to be conveyed efficiently to the distal region or end of the catheter while keeping the balloon flexible and without expansion in the balloon wrapping size, and highly penetrable through the stricture site, as the accordion phenomenon of the balloon and the inner shaft is prevented and the favorable inflation/deflation response of balloon is preserved simultaneously.

BRIEF DESCRIPTION OF NUMERALS

Figure 1:
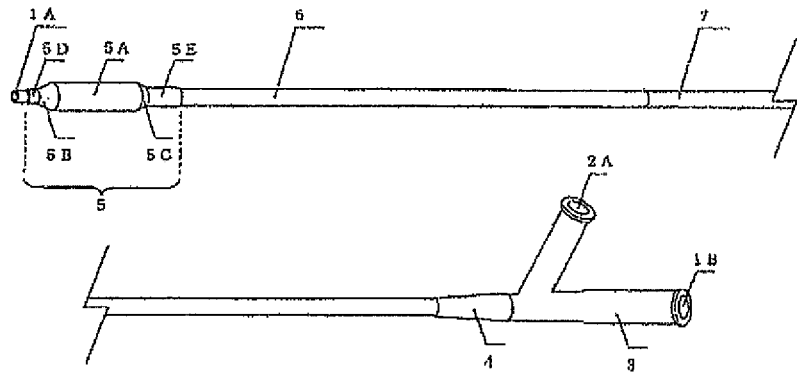
FIG. 1 is a schematic perspective view illustrating an over-the-wire catheter (OTW catheter) among common balloon catheters.

1. Guide wire lumen
1A. Distal opening of guide wire lumen
1B. Proximal opening of guide wire lumen
2. Inflation lumen
2A. Inflation lumen opening
3. Hub
4. Strain relief
5. Balloon
5A. Straight tube region
5B. Distal tapered region
5C. Proximal tapered region
5D. Distal junction region
5E. Proximal junction region
6. Distal shaft
7. Proximal shaft
8. Inner shaft
9. Outer shaft
10. X-ray impermeable marker
11. Plate for peel test
11A. Balloon-fixing plate
11B. Balloon-holding plate
12. Adhesion member
13. Balloon sample for peel test
13A. Fixed balloon
13B. Balloon to be peeled off
14. Cylindrical film in the balloon straight tube region
15. Film for test of the modulus of the balloon in the axial direction
16. Artificial stricture site
17. Artificial blood vessel
18. Slide table
19. Guide wire
20. Catheter-holding unit
21. Force gauge
22. Hole
23. Catheter

BEST MODE OF CARRYING OUT THE INVENTION

Hereinafter, favorable embodiments of the balloon catheter according to the present invention will be described in detail with reference to drawings.

Figure 2:
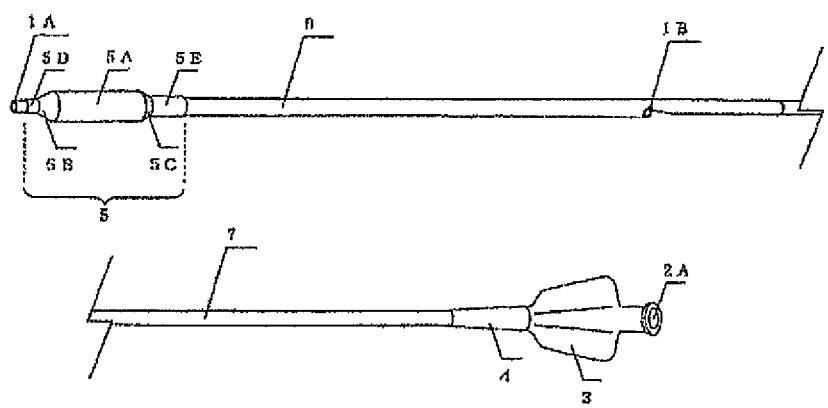
FIG. 2 is a schematic perspective view illustrating a high-speed exchange catheter (RX catheter) among common balloon catheters.

The catheter according to the present invention is a catheter having proximal and distal shafts respectively having proximal and distal end regions, wherein the distal end of the proximal shaft and the proximal end of the distal shaft are bound to each other, the proximal end of the proximal shaft is bound to an adapter member for holding the catheter, at least part of the distal shaft has an inner shaft and an outer shaft enclosing the inner shaft coaxially, the inner shaft extends out of the outer shaft toward the distal side, and the lumen of the inner shaft is coaxial type forming a guide-wire lumen, and the other structure is not particularly limited. Thus, the catheter may be an OTW catheter shown in FIG. 1 or an RX catheter shown in FIG. 2. Alternatively, it may have the other structure.

Figure 3:
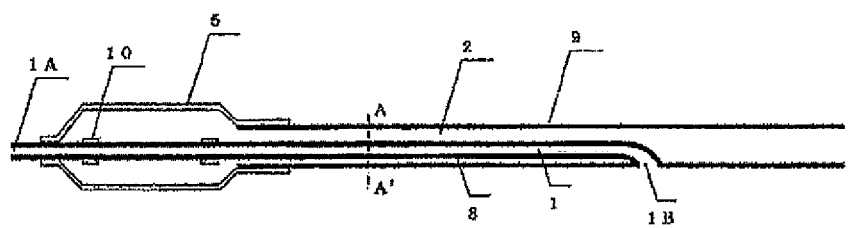
FIG. 3 is a schematic partial side view showing the vertical cross section of a common RX balloon catheter having a guide wire lumen region in the coaxial structure.
Figure 4:
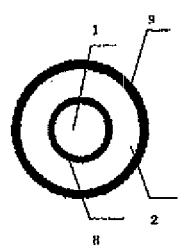
FIG. 4 is a crosssectional view of the catheter in FIG. 3 along the line A-A'.
Figure 5:
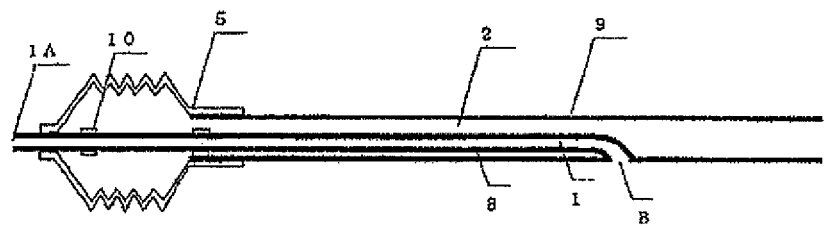
FIG. 5 is a schematic partial side view showing the vertical cross section of a common balloon catheter when the balloon is deformed into accordion-like shape.

In the case of a typical RX balloon catheter having a coaxial shaft such as that shown in FIG. 3, the cross section in the coaxial region has the structure shown in FIG. 4. To place a catheter such as that shown in FIG. 3 at a desirable treatment area, it is necessary to push the catheter forward by applying force to the adaptor member formed at the proximal end of the proximal shaft. When the route to the treatment area is bent in complicated way and the degree of stricture in the treatment area is high, the catheter cannot be pushed forward easily, demanding greater force. In such a case, the inner shaft and the outer shaft, which constitute at least part of the distal shaft, deform in a nested pattern, and, as a result, the balloon region may be deformed into accordion-like shape as schematically shown in FIG. 5. Such deformation increases the outer diameter of the balloon region, making the placement thereof in the treatment area more difficult.

Generally in the balloon region of a balloon catheter, the balloon is wrapped around the inner shaft for reduction in profile as much as possible, for improvement in convenience of operation during insertion of the catheter to the treatment area from outside. The catheter according to the present invention retains its wrapped shape and the balloon region becomes resistant to accordion-like deformation even when the catheter is applied under an insertion force of a particular value or more due to strength inherent to the material of the wrapped balloon and also due to the adhering force of the contact surface between the balloon surfaces in contact with each other as wrapped around the inner shaft. Specifically in regard to the adhering force above, the peeling strength when two balloons adheres to each other is characteristically 0.06 N or more, and in regard to the strength inherent to the balloon, the modulus of the balloon in the axial direction is characteristically 100 N/mm$^2$ or more. As a result, it becomes possible simultaneously to convey the force applied to the adapter member effectively to the catheter distal end and improve the efficiency of locating the catheter in the treatment area.

Figure 6:
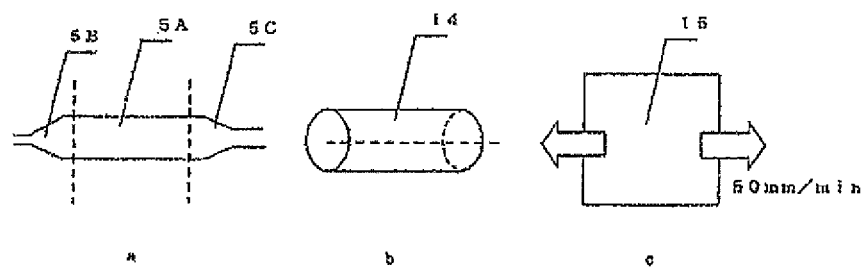
FIG. 6 is a schematic view illustrating the sample used in measurement of the modulus in the axial direction of the balloon according to the present invention.

In the present invention, the modulus of the balloon in the axial direction is a modulus of the balloon straight tube region in the longitudinal direction. As shown in FIG. 6.a, both ends of the straight tube region are cut to give a cylindrical film like the one shown in FIG. 6.b, and the resulting cylindrical film is cut additionally along the dotted line of FIG. 6.b into a single film as shown in FIG. 6.c, and then the modulus thereof is determined by using a tensile strength tester.

Figure 7:
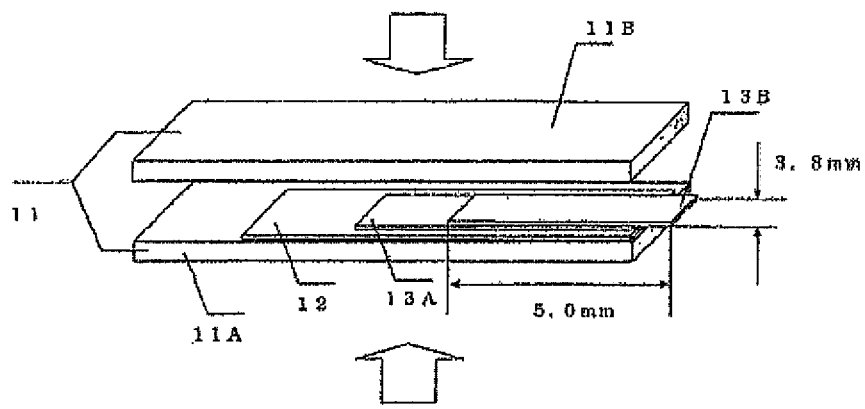
FIG. 7 is a schematic view of the sample used in the peel test of the present invention before heat treatment.
Figure 8:
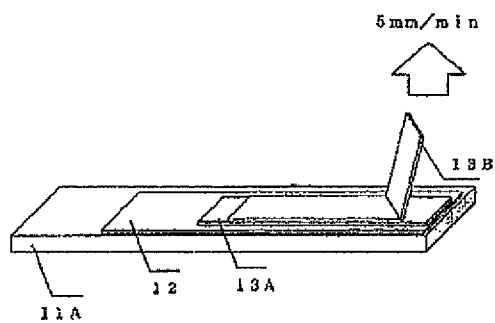
FIG. 8 is a schematic view of the sample used in the peel test of the present invention during evaluation of its peeling force.

In the present invention, the peeling strength is the maximum strength as determined while a balloon is processed into a film shape as shown in FIG. 7 to form two balloon samples of 3.8 mm×5.0 mm and the two balloon samples adhering to their outer surfaces facing each other, and one of the adhering balloons is pulled in a direction perpendicular to the test sample in a tensile strength tester as shown in FIG. 8.

The peeling strength is determined by using a sample obtained by fixing one balloon sample on a test plate tightly, for example with an adhesive member, the other balloon sample being adhered thereto, holding the both sides with test plates, and heat-treating the test sample in the fixed state at a temperature of 55° C. for one hour.

Although it is possible to obtain the advantageous effects of the present invention at a peeling strength of 0.06 N or more and a modulus of the balloon in the axial direction of 100 N/mm$^2$ or more, excessively large peeling strength may lead to damage of the balloon when the wrapped balloon is inflated for unwrapping at the treatment area, and thus, the peeling strength is preferably 1.00 N or less for prevention thereof and more preferably 0.75 N or less for prevention of separation of the coated hydrophilic resin. Since the inflated balloon region should also be flexible enough to be recrossed in the lesion area, the modulus of the balloon in the axial direction is preferably 250 N/mm$^2$ or less.

Balloon materials having a varying peeling strength and modulus of the balloon in the axial direction are used depending on the lesion area and the purpose of treatment, and thus, a resin composition is preferably coated on the outer surface of the balloon material for obtaining the advantageous effects of the invention. In addition, a hydrophilic resin lubricating when wet is preferably coated for improvement in insertion efficiency by reduction in friction between the catheter and the vascular wall during operation of the catheter in the living blood vessel. The hydrophilic resin film more preferably has a bilayer coat structure consisting of an undercoat layer containing a urethane resin and a topcoat layer containing a hydrophilic resin from the viewpoint of durability of hydrophilic coating.

Moreover, the resin film preferably has a layer of a urethane-base polymer consisting of 40 to 80 wt % of at least one of aromatic diisocyanates, aliphatic diisocyanates, and alicyclic diisocyanates and 20 to 60 wt % of at least one trifunctional polyol, and a surface hydrophilic polymer layer of a polyalkylene glycol and/or a monomethoxypolyalkylene glycol formed on the urethane-based polymer layer.

The content of the diisocyanate component in the urethane resin layer is 40 wt % or more and 80 wt % or less, preferably 45 wt % or more and 75 wt % or less, and more preferably 50 wt % or more and 70 wt % or less. An isocyanate content of less than the range above is not preferable, from the viewpoint of safety to the body, in that adhesive strength to the base material and the hydrophilic polymer layer deteriorates and hardening speed of the urethane resin reduces, which in turn demands additional heat treatment, affecting the mechanical properties of the base material, or addition of a commonly used catalyst such as amine or tin compound for adjustment of the hardening velocity. An isocyanate content higher than the range above is also unfavorable because the urethane resin becomes brittle.

A trifunctional or higher polyol is used in combination with the isocyanate compound in forming the polyurethane-based polymer layer. Use of a bifunctional or lower polyol is unfavorable because it leads to deterioration in the adhesive strength of the polyurethane-based polymer layer. Use of a water-soluble polyol is also unfavorable because increase in volume of the polyurethane-based polymer layer by swelling may inhibit insertion of catheter, when used in a medical device by which a catheter is inserted into a stricture site.

Examples of the trifunctional or higher polyols for the polyurethane-based polymer layer include polyester-based polyols, polyether polyols such as poly(oxypropyleneether) polyols and poly(oxyethylene-propylene ether)polyols, polymer polyol branched derivatives such as acrylic polyols, castor oil and the derivatives thereof, glycerin, trimethylolpropane, trimethylolethane, 1,2,6-hexanetriol, pentaerythritol, sorbitol, mannitol, and the like.

The resin coating on the balloon outer surface is not limited to hydrophilic resin coating, and a hydrophobic resin may be coated according to the treatment area and the treatment purpose, if the phenomenon called slipping of the balloon slipping off from the treatment area during dilation of balloon is prevented, and thus, any other coating may be used without particular restriction in the present invention.

If no resin coating is carried out on the balloon outer surface, the balloon outer surface is preferably made of a polyamide elastomer resin composition having a durometer hardness of 55 D or less, and for more efficient prevention of the accordion-like deformation, use of a polyamide elastomer resin composition having a durometer hardness of 40 D or less is more preferable. It is because, in the case of using a polyamide elastomer, the elastomer having a hardness of 55 D or less lead to increase in the content of soft segment, increase in adhering strength, and consequently increase in peeling strength. If the properties of the balloon such as compression strength and compliance characteristics demanded for the balloon are not satisfied with the polyamide elastomer resin having a durometer hardness within the range above, the balloon is preferably formed in the multi-layer structure. The outer and inner layers forming the multi-layer structure are preferably made of the same polyamide elastomer resin because the risk of separation of the outer and inner layers of balloon is minimal. The catheter structure and the balloon shape of the means described above do not restrict the advantageous effects of the present invention. Thus, the structure of the means above may be coaxial or biaxial, and the multi-layer structure of the balloon may be a two-layer, three-layer, or higher layered structure. The resin material for the outer or inner layers in the multilayer structure may be a resin composition other than the polyamide elastomer.

The balloon is produced, for example, by dip molding or blow molding, and a suitable method is selected according to application. In the case of a balloon catheter for vasodilation of the stricture site of cardiac coronary, use of blow molding is preferable for sufficient pressure resistance. One example of method of preparing a balloon by blow molding will be described below. First, a tubular parison in arbitrary dimension is formed for example by extrusion molding. The tubular parison is placed in a metal mold having a shape corresponding to the balloon shape, forming a balloon having the shape identical with that of the mold by stretching it in the axial and diameter directions by biaxial stretching step. The biaxially stretching step may be carried out under heated condition for multiple times. The stretching in the axial direction may be preformed simultaneously with or before or after stretching in the diameter direction. The balloon may be annealed additionally for stabilization of its shape and dimension.

Generally, a balloon has a straight tube region, connecting regions at the distal and proximal sides, and tapered regions between the straight tube region and the connecting regions. In the present invention, the dimension of the balloon is determined according to the application of the balloon catheter, but the outer diameter of the straight tube region when dilated is from 1.00 mm to 35.00 mm, preferably from 1.26 mm to 30.00 mm, and the length of the straight tube region is from 5.00 mm to 150.00 mm, preferably from 5.00 mm to 120.00 mm.

The method of processing a balloon into a balloon catheter is, for example, adhesion with an adhesive or fusion lithe material is a combination of thermoplastic materials. When an adhesive is used, the composition, chemical structure, and hardening mode thereof are not limited. Thus, adhesives such as of a urethane, silicone, epoxy, or cyanoacrylate resin are preferably used from the viewpoints of composition and chemical structure, and adhesives such as of two-liquid mixing, UV-hardening, water hardening, thermally hardening are used preferably from the viewpoint of hardening mode. When an adhesive is used, use of an adhesive having a post-hardening hardness prohibiting discontinuous change in rigidity in the region before and after the connection region is preferable, and the adhesive may be selected according to the material, dimension, rigidity of the connection region, and the like. The connection region may be heat-treated for reduction in diameter of the connection region, and if a material less adhesive such as polyolefin is used, the connection region may be plasma-processed before adhesion, for example with oxygen gas, for improvement in adhesiveness.

For connection by fusion, a, core material in any dimension and shape may be inserted into the tube for the outer shaft, for making a desirable lumen. In such a case, considering removal of the core material after completion of the processing, a fluorine resin such as of polytetrafluoroethylene, poly-para-xylylene, polymonochloro-para-xylylene, or the like is preferably coated on the outer surface of the core material, for easier removal of the core material. The dimension and the crosssectional shape of the core material are not particularly limited, if the advantageous effects of the present invention are obtained, and may be determined according to the processability during processing, the crosssectional area of the desirable lumen, and the like.

The material for the distal shaft, i.e., for the inner shaft or the outer shaft, is not particularly limited. Examples of the materials for the inner shaft include polyolefin, polyolefin elastomers, polyester, polyester elastomers, polyamide, polyamide elastomers, polyurethane, polyurethane-elastomers, and the like. Since the lumen of the inner shaft forms a guide wire lumen, polyethylene, in particular a high-density polyethylene, is preferable considering the slidability of the guide wire; and it is more preferable to make at least part of the inner shaft have a multi-layered structure by forming the innermost layer with high-density polyethylene and the outermost layer with a material fusable with balloon or the outer shaft. In addition, the lumen of the inner shaft may be coated, for example, with polydimethylsiloxane for improvement in slidability of the guide wire.

The material for the outer shaft is not particularly limited either. Examples thereof include polyolefin, polyolefin elastomers, polyester, polyester elastomers, polyamide, polyamide elastomer, polyurethane, polyurethane elastomers, and the like.

Similarly, the material for the proximal shaft is also not particularly limited, but the material for the proximal shaft preferably has rigidity similar to or higher than that of the distal shaft. From the viewpoints of processability, safety to the body, and others, metals such as stainless steel, high-rigidity resin materials such as polyimide, polyamide-imide, and polyether ether ketone, and the like are preferably used. For continuous distribution of the rigidity of the catheter in the length direction, the rigidity of the distal side of the proximal shaft may be made lower than that of the proximal side of the proximal shaft, by forming spiral cut, groove, slit, or the like at the distal side of the proximal shaft.

Examples of the materials preferable for the adapter member include resins such as polycarbonate, polyamide, polyurethane, polysulfone, polyarylate, styrene-butadiene copolymers, polyolefin, and the like.

A core wire may be placed in the catheter for improvement in convenience of the operation of inserting the catheter along the guide wire from outside, efficient transmission of the force applied to the catheter to the distal end, and prevention of catheter kink (twist) in the balloon catheter according to the present invention. The core wire may be placed in any region of the catheter, but preferably placed in a lumen other than the guide wire lumen for convenience of operation of inserting the catheter along the guide wire. Part of the outer diameter of the core wire may be tapered in the direction toward the distal end to make the distribution in rigidity of the catheter in the length direction more uniform. The core wire is not particularly limited if it is a metal. The material for the core wire is determined according to the material and the application of the catheter, but preferably a stainless steel alloy, a cobalt-chromium alloy, or a nickel-titanium alloy, from the point of processability or safety to the body. The method of processing the core wire is also not particularly limited, and methods such as centerless grinding are used preferably.

An X-ray impermeable marker may be installed to make a particular unit of the catheter more visible and locate the catheter more easily during treatment with the catheter according to the present invention. The X-ray impermeable marker is not limited if it is a X-ray-impermeable material, and the kind of the material such as metal or resin is not limited. The site and the number thereof formed are not limited either, and are determined according to the application of the catheter.

In the balloon catheter according to the present invention, the pressure at which the balloon folding is removed is preferably 0.6 atmG or more. The pressure at which the balloon folding is removed is a pressure when the wrapping of the balloon region around the inner shaft is removed after the balloon region is immersed in water at a temperature of 37° C. for 30 seconds and then, water pressure is applied from the adapter member into the balloon. If the pressure at which the balloon folding is removed is 0.6 atmG or more, it is possible to obtain the advantageous effects of the present invention, but if the pressure thereof is excessively high, the balloon may be damaged before the wrapped balloon is inflated and unwrapped in the treatment area. Thus, the pressure at which the balloon folding is removed is preferably 2.0 atmG or less for prevention thereof and more preferably 1.6 atmG or less for prevention of separation of the coated hydrophilic resin.

EXAMPLES

Hereinafter, Examples and Comparative Examples of the present invention will be described in detail, but it should be understood that the present invention is not limited to the following Examples.

Example 1

A tubular parison in almost circular inner and outer shape (outer diameter: 0.44 mm, inner diameter: 0.20 mm) was prepared by extrusion molding using a polyamide elastomer having a durometer hardness of 70 D (trade name: PEBAX7033SA01: manufactured by Arkema). The parison was then processed in biaxially stretching blow molding using a balloon-forming metal mold to give a balloon having a straight-tube-region outer diameter of 1.50 mm and a straight-tube-region length of 100 m. A tube (outer diameter: 0.56 mm, inner diameter: 0.42 mm) was prepared by extrusion molding using a high-density polyethylene resin (HY540, Japan Polychem Corp.) as the balloon-catheter inner shaft tube, while a tube having an outer diameter of 0.88 mm and an inner diameter of 0.71 mm was prepared by extrusion molding using a polyamide elastomer (trade name: PEBAX7233A01: manufactured by Arkema) as the outer shaft tube. An OTW balloon catheter in the coaxial structure was prepared with these tubes and an adapter member prepared by injection molding by using a polycarbonate resin (Makloron2658, Bayer).

The balloon catheter was dipped in a solution of 5 g of 4,4-diphenylmethane diisocyanate and 5 g of polypropylene glycol having an average molecular weight of 1000 dissolved in 40 g of tetrahydrofuran and dried at 50° C. for 10 minutes to form an undercoat layer. The balloon catheter was then dipped in a solution of 10 g of polyethylene glycol having an average molecular weight of 20,000 dissolved in 40 g of ethanol and dried at 50° C. for 15 minutes to form a hydrophilic topcoat layer in order to give a lubricant-coated balloon catheter.

The test sample shown in FIG. 7 was prepared with the catheter and heat-treated at 55° C. for 1 hour, and the peel test of the sample was carried out in a tensile strength tester, as the balloon shown in FIG. 8 was pulled at a rate of 5 mm/min in the direction perpendicular to the test sample (arrow direction in FIG. 8). The modulus of the balloon in the axial direction was also determined in the tensile strength tester, at a tensile rate of 50 mm/min using the test sample shown in FIG. 6. As a result, the peeling strength and the modulus of balloon in the axial direction were respectively 0.17 N and 104 N/mm$^2$.

Figure 10:
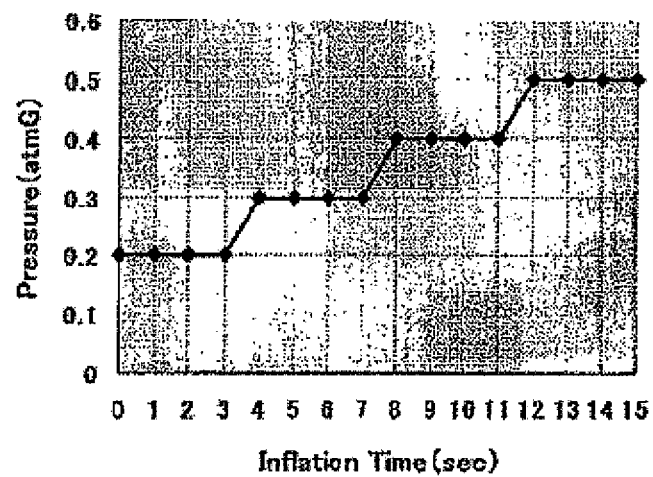
FIG. 10 is a graph showing the pressurization condition when the pressure at which the balloon folding is removed is evaluated in the test for evaluating the pressure when the folding of the balloon according to the present invention is removed.

Separately, the balloon region of the balloon catheter obtained was wound around the inner shaft; a balloon protection tube was placed around the balloon for prevention of separation; and the composite was disinfected with ethyleneoxide gas (EOG), to give a sample for measurement of the pressure at which the balloon folding is removed. Air on the inflation lumen of the test sample was replaced with water in advance; the test sample was left in water at 37° C. for 30 seconds; the sample in water was pressurized through the adapter member by a leak tester, and the pressure when the balloon folding is removed was determined. The sample was pressurized according to the pressurization condition program shown in FIG. 10. Specifically, the initial pressure was 0.2 atmG; the pressure was increased stepwise by 0.1 atmG at a pressurization rate of 0.1 atmG/sec, while the pressure after each pressurization is held for 3 seconds. Although the maximum pressure shown in FIG. 10 is 0.5 atmG for explanation of the pressurization pattern, it is needless to say that the pressure was raised and held stepwise until the balloon folding was removed. As a result, the pressure at which the balloon folding was removed was 1.6 atmG.

Example 2

A balloon catheter having a straight-tube-region outer diameter of 1.50 mm and a straight-tube-region length of 100 mm was prepared using the materials identical in size and shape with those used in Example 1.

The balloon catheter was then dipped in a solution of 15 g of 4,4-diphenylmethane diisocyanate and 15 g of polypropylene glycol having an average molecular weight of 1000 dissolved in 40 g of tetrahydrofuran 40 g and dried at 50° C. for 10 minutes, to form an undercoat layer. The balloon catheter was then dipped in a solution of 30 g of polyethylene glycol having an average molecular weight of 20,000 dissolved in 40 g of ethanol and dried at 50° C. for 15 minutes to form a hydrophilic topcoat layer in order to give a lubricant-coated balloon catheter. The peeling strength of the catheter, the modulus of the balloon in the axial direction and also the pressure at which the balloon folding was removed were determined in the same manner as Example 1. The peeling strength was 0.72 N, the modulus of the balloon in the axial direction was 115 N/mm$^2$, and the pressure at which the balloon folding was removed was 1.4 atmG.

Example 3

A balloon having a straight tube region of 1.50 mm and a straight-tube-region length of 100 mm was prepared using a tubular parison (outer diameter: 0.46 mm, inner diameter: 0.22 mm) of a polyester elastomer having a durometer hardness of 72 D (trade name: Hytrel 7277: manufactured by Du Pont-Toray). A lubricant-coated balloon catheter was prepared in a manner similar to Example 1, except that the balloon above was used. The peeling strength of the catheter, the modulus of the balloon in the axial direction, and the pressure at which the balloon folding was removed were determined in the same manner as Example 1. The peeling strength was 0.16 N, the modulus of the balloon in the axial direction was 121 N/mm$^2$, and the pressure at which the balloon folding was removed was 1.2 atmG.

Example 4

A bilayer balloon having a straight tube region of 1.50 mm and a straight-tube-region length of 100 mm was prepared by using a tubular parison (outer diameter: 0.48 mm, inner diameter: 0.20 mm) consisting of an outer layer of polyamide elastomer having a durometer hardness of 55 D (trade name: PEBAX5533SA01: manufactured by Arkema) and an inner layer of a polyamide elastomer having a durometer hardness of 70 D (trade name: PEBAX7033SA01: manufactured by Arkema), and an OTW balloon catheter in the coaxial structure was prepared in the same manner as Examples 1 and 2. No resin coating, for example with a hydrophilic resin, was carried out. The peeling strength of the catheter, the modulus of the balloon in the axial direction and the pressure at which the balloon folding was removed were determined in the same manner as Example 1. The peeling strength was 0.06 N, the modulus of the balloon in the axial direction was 112 N/mm², and the pressure at which the balloon folding was removed was 0.6 atmG.

Comparative Example 1

A balloon and balloon catheter having a straight-tube-region outer diameter of 1.50 mm and a straight-tube-region length of 100 mm were prepared using the materials identical in size and shape with those used in Example 1. No resin coating, for example with a hydrophilic resin, was carried out. The peeling strength of the catheter, the modulus of the balloon in the axial direction and the pressure at which the balloon folding was removed were determined, in the same manner as Example 1. The peeling strength was 0.01 N, the modulus of the balloon in the axial direction was 110 N/m², and the pressure when the balloon folding was removed was 0.2 atmG.

Comparative Example 2

A tubular parison (outer diameter: 0.33 mm, inner diameter: 0.20 mm) in almost circular inner and outer shapes was prepared by extrusion molding using a polyamide elastomer having a durometer hardness of 70 D (trade name: PEBAX7033SA01: manufactured by Arkema). The parison was then processed in biaxially stretching blow molding using a balloon-forming metal mold to give a balloon having a straight-tube-region outer diameter of 1.50 mm and a straight-tube-region length of 100 mm. A lubricant-coated balloon catheter was prepared in a manner similar to Example 1 except that the balloon above was used. The peeling strength of the catheter, the modulus of the balloon in the axial direction and the pressure at which the balloon folding was removed were determined in the same manner as Example 1. The peeling strength was 0.16 N, the modulus of the balloon in the axial direction was 84 N/mm², and the pressure at which the balloon folding was removed was 1.2 atmG.

Comparative Example 3

A balloon catheter having a straight-tube-region outer diameter of 1.50 mm and a straight-pipe-region length of 100 mm was prepared using the materials identical in size and shape with those used in Example 3. No resin coating, for example with a hydrophilic resin, was carried out. The peeling strength of the catheter, the modulus of the balloon in the axial direction and the pressure when the balloon folding was removed were determined in the same manner as Example 1. The peeling strength was 0.01 N, the modulus of the balloon in the axial direction was 119 N/mm², and the pressure at which the balloon folding was removed was 0.2 atmG.

Comparative Example 4

A tubular parison (outer diameter: 0.60 mm, inner diameter: 0.20 mm) in almost circular inner and outer shapes was prepared by extrusion molding by using a polyurethane-elastomer having a durometer hardness of 90 A (trade name: Tecoflex: manufactured by Thermedics Inc.). The parison was then processed in biaxially stretching blow molding using a balloon-forming metal mold to give a balloon having a straight-pipe-region outer diameter of 2.50 mm and a straight-pipe-region length of 15 mm. A lubricant-coated balloon catheter was prepared similarly to Example 2 except the balloon above was used. The peeling strength of the catheter, the modulus of the balloon in the axial direction, and the pressure at which the balloon folding was removed were determined in the same manner as Example 1. The peeling strength was 1.01 N, the modulus of the balloon in the axial direction was 2.1 N/mm², and the pressure at which the balloon folding was removed was 2.0 atmG.

(Evaluation of Catheter)

Each of the catheters obtained in Examples 1 to 4 and Comparative Examples 1 to 4 was wound around an inner shaft in balloon under negative pressure, balloon protection tube was placed around it, and the catheter was disinfected with EOG to give a sample which was then evaluated in the following tests.

Figure 9:
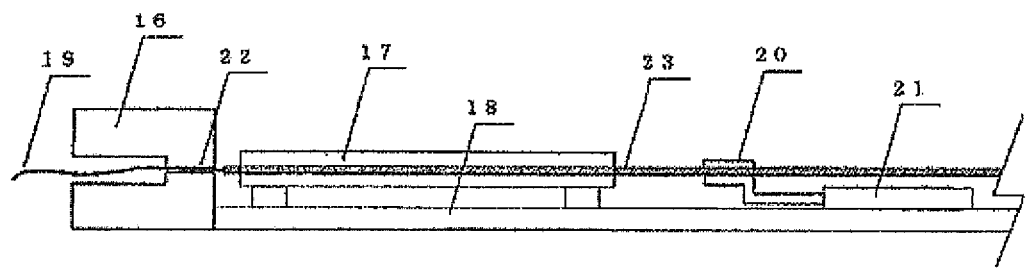
FIG. 9 is a schematic view illustrating a test system for evaluation of the catheter according to the present invention.

As shown in FIG. 9, a catheter was placed in an artificial blood vessel of polyethylene having an inner diameter of 3 mm and an outer diameter of 5 mm fixed on a slide table, and the catheter and a force gauge were connected to each other in the catheter-holding region. The distal end of the catheter was located 2 mm separated from artificial stricture site of stainless steel. A 0.014 inch guide wire was inserted into the guide wire lumen of catheter previously, and the guide wire located at a position more distal from the distal end of the catheter was inserted into the hole having a diameter of 0.45 mm formed at the artificial stricture site. The guide wire distal end was located at a position distal by 50 mm from the catheter distal end. The slide table was moved at a rate of 0.5 mm/sec until a load of 1.0 N was observed.

In the case of the catheters of Examples 1 to 4, no accordion-like deformation was observed in the balloon under a load of 1.0 N.

The balloon showed the accordion-like deformation when the load was 0.34 N, 0.85 N, 0.79 N, or 0.19 N in the catheter of Comparative Example 1, 2, 3, or 4, respectively, and it was not possible to apply a load higher than that.

In addition, the catheters of Examples 1 to 4 were less prone to problems such as deterioration in flexibility of balloon, increase in wrapping dimension, deterioration in balloon dilation/shrinkage responsiveness, and scattering of the balloon coating than those of Comparative Examples 1 to 4.

What is claimed is:
1. A balloon catheter having multiple tubular members, an adapter member connected thereto, a balloon for dilation of a constricted blood vessel, and a resin film on an outer surface of the balloon catheter, characterized in that a peeling strength of balloon surfaces when surfaces of the balloon adhere to each other in a state when the balloon is wrapped around at least one of the tubular members is 0.06 N or more and 1.00 N or less, and the modulus of the balloon in the axial direction is 100 N/mm² or more and 250 N/mm² or less,
  wherein the peeling strength is maximum strength as determined while two balloon samples having their outer surfaces facing each other and adhering to each other, and one of the balloon samples is pulled in a direction perpendicular to the other balloon sample in a tensile strength tester,
  wherein the resin film has a layer of a urethane-base polymer consisting of:

40 to 80 wt % of at least one of aromatic diisocyanates, aliphatic diisocyanates and alicyclic diisocyanates; and 20 to 60 wt % of at least one trifunctional polyol.

2. The balloon catheter according to claim 1, wherein the balloon is formed with a resin composition in a multi-layer structure.

3. The balloon catheter according to claim 1 or 2, wherein the balloon has a resin composition coated on an outer surface.

4. The balloon catheter according to claim 3, wherein the coated resin composition contains a hydrophilic resin that is lubricating when wet.

5. The balloon catheter according to claim 4, wherein the hydrophilic resin has at least two layers: an undercoat layer containing a urethane resin and a topcoat layer containing a hydrophilic resin.

6. A balloon catheter having multiple tubular members, an adapter member connected thereto, and a balloon for dilation of a constricted blood vessel, characterized in that a peeling strength of balloon surfaces when surfaces of the balloon adhere to each other in a state when the balloon is wrapped around at least one of the tubular members is 0.06 N or more and 1.00 N or less, and the modulus of the balloon in the axial direction is 100 N/mm$^2$ or more and 250 N/mm$^2$ or less, wherein the peeling strength is maximum strength as determined while two balloon samples having their outer surfaces facing each other and adhering to each other, and one of the balloon samples is pulled in a direction perpendicular to the other balloon sample in a tensile strength tester, wherein an outer surface of the balloon is made of a polyamide elastomer resin composition having a durometer hardness of 55 D or less.

7. The balloon catheter according to claim 1 or 2, wherein the pressure at which balloon folding is removed is 0.6 atmG or more.

* * * * *